United States Patent [19]
Fink et al.

[11] Patent Number: 6,161,434
[45] Date of Patent: Dec. 19, 2000

[54] METHOD AND DEVICE FOR DETECTING AND LOCATING A REFLECTING SOUND SOURCE

[76] Inventors: Mathias Fink, 16 rue Edouard Laferriére, 92190 Meudon; Jacques Lewiner, 7 avenue de Suresnes, 92190 Saint-Cloud, both of France

[21] Appl. No.: 09/202,392

[22] PCT Filed: Jun. 10, 1997

[86] PCT No.: PCT/FR97/01026

§ 371 Date: Jul. 16, 1999

§ 102(e) Date: Jul. 16, 1999

[87] PCT Pub. No.: WO97/47965

PCT Pub. Date: Dec. 18, 1997

[30] Foreign Application Priority Data

Jun. 13, 1996 [FR] France ................................. 96 07359

[51] Int. Cl.[7] ............................................... G01N 29/14
[52] U.S. Cl. .............................. 73/587; 73/602; 73/592
[58] Field of Search ........................... 73/587, 592, 602, 73/626, 628; 367/103, 105

[56] References Cited

U.S. PATENT DOCUMENTS

| | | | |
|---|---|---|---|
| 4,592,034 | 5/1986 | Sachse et al. | 367/127 |
| 5,092,336 | 3/1992 | Fink | 128/660.03 |
| 5,428,999 | 7/1995 | Fink | 73/599 |
| 5,431,053 | 7/1995 | Fink | 73/602 |

FOREIGN PATENT DOCUMENTS

| | | |
|---|---|---|
| 0 383 650 | 8/1990 | European Pat. Off. . |
| 2 262 303 | 9/1975 | France . |

OTHER PUBLICATIONS

C. Prada, et al., "The iterative Time reversal Mirror : a solution to self–focusing in the pulse echo mode", *Journal of the Acoustical Society of America*, vol. 90, No. 2, Aug. 1991, pp. 1119–1129.

M. Fink, "Time Reversal of Ultrasonic Fields—Part I: Basic Principles", *IEEE Transactions on Ultrasonics Ferroelectrics and Frequency Control*, vol. 39, No. 5, Sep. 1992, pp. 555–566.

*Primary Examiner*—John E. Chapman
*Attorney, Agent, or Firm*—Marshall, O'Toole, Gerstein, Murray & Borun

[57] ABSTRACT

During a passive initial stage, acoustic signals received by a receiving transducer array are recorded, and the corresponding electric signals are stored. To search for the possible presence of a sound source whose contribution to the signal recorded in the passive initial stage may be faint, window of each electric signal stored in the initial stage is time reversed and amplified to produce excitation signals which are applied to emitting transducers of an array corresponding to that of the receiving transducers. The acoustic echo signals received by the receiving transducers are recorded, and the corresponding electric signals are stored, and can be exploited to detect the possible presence of a reflecting sound source.

13 Claims, 3 Drawing Sheets

METHOD AND DEVICE FOR DETECTING AND LOCATING A REFLECTING SOUND SOURCE

BACKGROUND OF THE INVENTION

The present invention relates to a method and to a device allowing a sound source to be detected and/or located.

The present invention has many applications, among which mention may be made of the field of the non-destructive testing of solid objects by the methods referred to as acoustic emission, illustrations of which may be found in the work "Essais non destructifs. L'émission acoustique—Mise en oeuvre et applications" [Non-destructive tests. Acoustic emission—implementation and applications] by James Roget, AFNOR-CETIM, 1988.

In these acoustic emission methods, the object being studied is subjected to external stresses, which may be mechanical or thermal, and sensors around the object are used to detect possible cracking or micro-noise which are generated by these stresses and reveal structural defects of the object. One difficulty with these methods is that the level of the signal representing a defect may be very low and hard to distinguish from the background noise which accompanies it.

The invention applies more generally to the detection of sound sources which may be of low absolute or relative level, in the signal collected by acoustic sensors. The acoustic propagation medium should not be understood as being limited to solids. It may also be fluid (liquid or gas) or contain interfaces.

In order to overcome the limitation of passive methods of sound source location in the presence of a low signal-to-noise ratio, it is known to combine them with correlation and/or triangulation techniques in order to search for the sources and identify them.

However, these techniques also have limitations. On the one hand, if the propagation medium causes a great deal of perturbation (refraction, multiple reflections, etc.) for acoustic waves, the various sensors of the array receive acoustic signals which have lost all correlation, which makes it almost impossible to detect and locate the sound source precisely. On the other hand, in a very noisy environment (for example a flowing fluid or the marine environment), the signal to noise ratio may be so small that it remains impossible to detect and locate the sound source even with sophisticated correlation calculations.

A method is furthermore known (EP-A-0,383,650 or U.S. Pat. No. 5,092,336) for detecting and locating a reflecting target, according to which the medium is illuminated from at least one transducer emitting a beam referred to as the illumination beam, the signals reflected by the medium are collected using a plurality of transducers belonging to an array, and they are stored; the echoes coming from a determined zone of the medium are selected by windowing; the signals are time reversed and are re-emitted; and the above operations are repeated. In this method, the target possibly detected is generally the most highly reflecting object in the zone in question (calculus in the case of lithotripsy applications, structural defects in the case of non-destructive testing, etc.). If a plurality of reflecting objects contribute to the measured signal, one or more iterations of the process allow selective focusing on the target.

This method gives an already considerable improvement in the detection and location capacities, particularly in media having spatial variations in the acoustic properties such as the speed of the waves (see "Time Reversal of Ultrasonic Fields—Part I: Basic Principles", by M. Fink, IEEE Trans. on UFFC, Vol. 39, No. 5, September 1992, pages 555–566). Under certain conditions, however, the illumination which the illumination beam produces at the target may not be sufficient to produce reflection which is strong enough to be detectable by the array of sensors. On account of this limitation, provision is generally made for the illumination beam to be a brief pressure pulse, allowing wavefront or pulse echo detection in the collected signal (see EP-A-0, 591,061 or U.S. Pat. No. 5,428,999). However, this arrangement may be insufficient, in particular when the signal-to-noise ratio is very low, or when there are large aberrations between the transducers and the target.

Furthermore, it could in certain cases happen that the target of interest is not the most highly reflecting object in the explored zone. In such cases, the known methods with time reversal may fail. For example, in non-destructive testing, the contribution from a structural defect to the echo signals may be fully drowned in those from the surfaces or interfaces of the article being examined, this problem requiring special arrangements such as those described in EP-A-0,541,434 or in U.S. Pat. No. 5,431,053.

When the target of interest is a sound source, it is not necessarily the most highly reflecting object in its environment, which limits the effectiveness of the known methods with time reversal in overcoming the deficiencies of the passive listening methods. For example, if hydrophones are used to search for the location of a gas leak along a sub-marine gas pipeline, the gas pipeline section containing the leak will not a priori be more highly reflecting than the other sections.

The object of the present invention is, in particular, to provide a method for detecting and/or locating a sound source which meets practical requirements better than those previously known, in particular in so far as it allows a source to be detected in a noisy medium and/or one exhibiting reflections and multiple refractions which defeat the prior methods.

SUMMARY OF THE INVENTION

The invention thus provides a method of detecting and/or locating a sound source, comprising a passive initial step in which acoustic signals received by reception transducers of a first array are acquired, and electric signals produced by the reception transducers of the first array in response to the said acoustic signals are stored. The method then comprises the following steps:

(a) at least one time window of each electric signal stored in the passive initial step is time reversed and amplified in order to produce excitation signals;

(b) the excitation signals are applied to respective emission transducers of a second array spatially corresponding to the first array;

(c) acoustic echo signals received by the reception transducers of a third array are acquired, and electric signals produced by the reception transducers of the third array in response to the said acoustic echo signals are stored; and (d) the electric signals stored in step (c) are used to detect the possible presence of a reflecting sound source.

In a typical embodiment, the "first", "second" and "third" arrays are merged and consist of transducers operating in reception and in emission.

The invention uses the fact that the sound signals returned during step (b) are subjected to the same propagation conditions as the sound signals received during the initial passive step, in so far as the relative position of the source and the array of transducers is not too greatly modified between these steps, and in so far as the emission lobes are similar to the reception lobes. On account of this inverse path, the sound energy rendered during step (b) is concentrated on any source emitting a sufficient sound level. This source needs to be reflective in order to be detectable according to the invention. It is not, however, necessary for it to be the most highly reflecting object in the explored zone, in view of the focusing already carried out after the first emission by the second array of transducers. The aberrations are largely compensated for by virtue of the inverse path.

All the known methods for detecting and classifying reflecting sources can be used to exploit the measurements taken in step (c). For example, in a case in which the required sound source is of the pulse type, the possible presence of a signal peak on a plurality of reception channels may be looked for on these recordings. If such signal peaks do not visibly appear on the recordings, it is possible to look for correlations between the signals of different channels.

Such correlations may show up sources which are not directly visible. Any other known method of the same type may be used.

If, even under these conditions, a source is still drowned in the noise and therefore remains undetectable, it is possible to gain further sensitivity by providing that step (d) of using the electric signals measured in step (c) itself comprises one or more iterations of a process similar to the sequence of steps (a) to (c), that is to say including the following steps:

(e) at least one time window of each electric signal which has just been stored are time reversed and amplified in order to produce excitation signals;

(f) these excitation signals are applied to emission transducers of a fourth array spatially corresponding to the third array; and (g) acoustic echo signals received by reception transducers of a fifth array are acquired, and corresponding electric signals are stored.

The recordings thus obtained after one or more iterations can then be used, as indicated above, to detect the possible presence of a reflecting sound source.

Typically, the "fourth" and "fifth" arrays may be merged with the third.

The fact of providing recordings which correspond to two successive iterations allows a considerable improvement in the capacity for detection of a reflecting source. To this end, when the third and fifth arrays are merged, the following improvement is used, according to which, after having carried out steps (a) to (c) then n iterations ($n \geq 1$) of steps (e) to (g), an individual cross-correlation function $C_i^n(t)$ is evaluated, for at least some of the reception transducers of the third array, between the electric signal stored immediately before the n-th iteration and the electric signal stored at the end of the n-th iteration (step (g)), and the distribution of the individual cross-correlation functions thus evaluated is exploited.

One particularly advantageous method consists in constructing an overall cross-correlation function $C^n(t)$ by addition of the $C_i^n(t)$ over a certain number of channels:

$$C^n(t) = \sum_i C_i^n(t).$$

The presence of a reflecting sound source, even a weak one, then gives rise to a very pronounced peak in the correlation function $C^n(t)$.

In the above notation, the subscripts i refer to the channels, each relating to one of the reception transducers of the third array, and the superscripts refer to the ranks of the successive iterations.

Steps (a) to (c) may be considered to constitute an iteration n=0, even though the signals processed are of a different nature (passive listening and not echo measurement). In the case in which the first, third and fifth arrays coincide, as well as the second and fourth arrays, the electric signal produced by transducer i in step (c) or (g) of iteration $n \geq 0$ is written $R_i^{n+1}(t)$, and the electric signal produced by transducer i in the initial passive step is written $R_i^0(t)$.

The processing carried out in step (a) (n=0) or in step (e) (n>0) can then be expressed by:

$$E_i^n(t) = A_i^n \cdot S_i^n(T_i^n - t) \qquad (1)$$

the excitation signal $E_i^n(t)$ being, in step (b) or (f) following, applied to an emission transducer placed at the same location as the reception transducer i. In expression (1):

the signal $S_i^n(t)$ denotes the signal $R_i^n(t)$ multiplied by a predetermined windowing function $W_i^n(t)$;

$A_i^n$ denotes a predetermined amplification gain relating to channel i and iteration n (in general, the gains $A_i^n$ are the same for all the channels i: $A_i^n = A^n$)

$T_i^n$ denotes a delay needed for implementing the time reversal for causality reasons (in general, the delays $T_i^n$ will be the same for all the channels i: $T_i^n = T^n$).

The importance of the windowing must be emphasized. A windowing function $W_i^n(t)$ is generally defined as a zero weighting function outside a given time interval or window. The forms conventionally used in the field of acoustics may be employed for the $W_i^n(t)$: square-wave functions, Hamming functions, etc.

By choosing the positions of the time windows, it is possible to probe various regions of the medium, either at different distances or in different angular directions relative to the array(s) of transducers, by exploiting the delay laws of the propagation phenomena in a manner which is known per se.

It should be pointed out that, in the initial passive step, in step (c) and/or in steps (g), it may equally well be the signals $R_i^n(t)$ or the windowed and weighted signals $S_i^n(t) = R_i^n(t) \cdot W_i^n(t)$ which are stored, this being no more than an implementation choice with no major consequence on the way in which the method is carried out.

The calculation of the individual cross-correlation functions $C_i^n(t)$, when it is employed, may also include the windowing functions $W_i^n(t)$:

$$C_i^n(t) = \int_{-\infty}^{+\infty} S_i^n(u) \cdot S_i^{n+1}(u+t) du \qquad (2)$$

It will be understood that the formula (1) indicated above is given to assist explanation, and that a variety of variants may be made to it without departing from the scope of the invention, for example:

the amplification may be dependent on frequency. In other words, the multiplication by a gain $A_i^n$ could be replaced by amplification/filtering with a transfer function $A_i^n(f)$, f denoting the frequency of the sound. The form of the transfer functions which are used can be optimized according to the type of application of the method. Such frequency-dependent amplification may, for example, be used to compensate for possible differences between the emission lobes and the reception lobes of the transducers, in particular when different transducers are used in emission and in reception.

it is possible for the signals measured by the reception transducers or the excitation signals to be spatially interpolated, in a manner which is known per se, in order to account for a shift between the array of the emission transducers and the array of the reception transducers. Such a shift may be due to the fact that the emission and reception transducers are separate, or else to motion of the array between reception and subsequent re-emission.

it is also possible, in step (b), to re-emit waves with higher frequency than those acquired in the initial passive step, which makes it possible to locate more accurately a reflecting source which emits principally at low frequencies. In this case, in a formula such as for (1), and for n=0 only, the time reversal is carried out in the form $S_i^n(T_i^n-\alpha.t)$, $\alpha$ being a coefficient greater than 1 corresponding to the desired frequency ratio.

It is then suitable to provide that the second array of emission transducers corresponds to the first array of reception transducers through a homothetic transformation of ratio $1/\alpha$.

The sound emission acquired during the initial passive step may be internal to the source. This case is, for example, that of a crack in an article subjected to non-destructive testing by acoustic emission, or a leak along a gas pipeline placed on the seabed.

In the first case, the sound emission is connected to mechanisms such as twinning, fracture or microcleavage produced via mechanical stress in metallic materials, or by fractures of fibres in composite materials.

In the second case, the sound emission is connected with the rubbing noise, the turbulence and the generation of bubbles, near to the crack.

The sound emission may also be due to an interaction of the source with the surrounding medium. This is, for example, the case of aerodynamic or hydro-dynamic noise when there is relative motion between the source and the medium in which it is found.

When there is, in the surrounding medium, ambient acoustic noise not generated by the arrays of transducers, the character of the sound from the reflecting source may also be combined with the modification of this ambient acoustic noise by the source itself (reflection or absorption or screen effect).

The invention is applicable whether the emission is continuous or intermittent.

If the array is mobile relative to the source or the medium, but indeformable, a time reversed signal, obtained from a weighted average of the signals received by various neighbouring reception transducers, may advantageously be applied to the emission transducers during each emission step, the weighting coefficients being determined on the basis of the spacing of the transducers and the speed at which the array moves.

The passband of the transducers will be chosen on the basis of the nature of the required sound sources and of the propagation medium.

For the detection of noise sources in solids during non-destructive testing by acoustic emission, a frequency range between about 100 kHz and about 10 MHz, for example around 500 kHz, will in general be used.

For the detection of reflecting sound sources in air, a range of frequencies between a few Hz and a few tens of kHz will in general be used.

For the detection of reflecting sources in a liquid medium, for example a sea environment, a frequency range having a lower limit of a few hertz, for example 3 Hz, and an upper limit of a few hundreds of kHz, for example 200 kHz, will in general be used. Transducers having such a passband are already used, in particular for seismic or sub-marine detection.

High amplification is necessary during step (a) or (e) when attempts are being made to detect over large distances. This amplification will often be from about one hundred to several hundreds. It may then lead to the use of emission transducers separate from the reception transducers. The transducers may, advantageously but without implying limitation, be chosen so as to have comparable emission and reception lobes, possible differences being at least in part capable of being compensated for by filtering, as indicated above.

DESCRIPTION OF PREFERRED EMBODIMENTS

Figure 1:
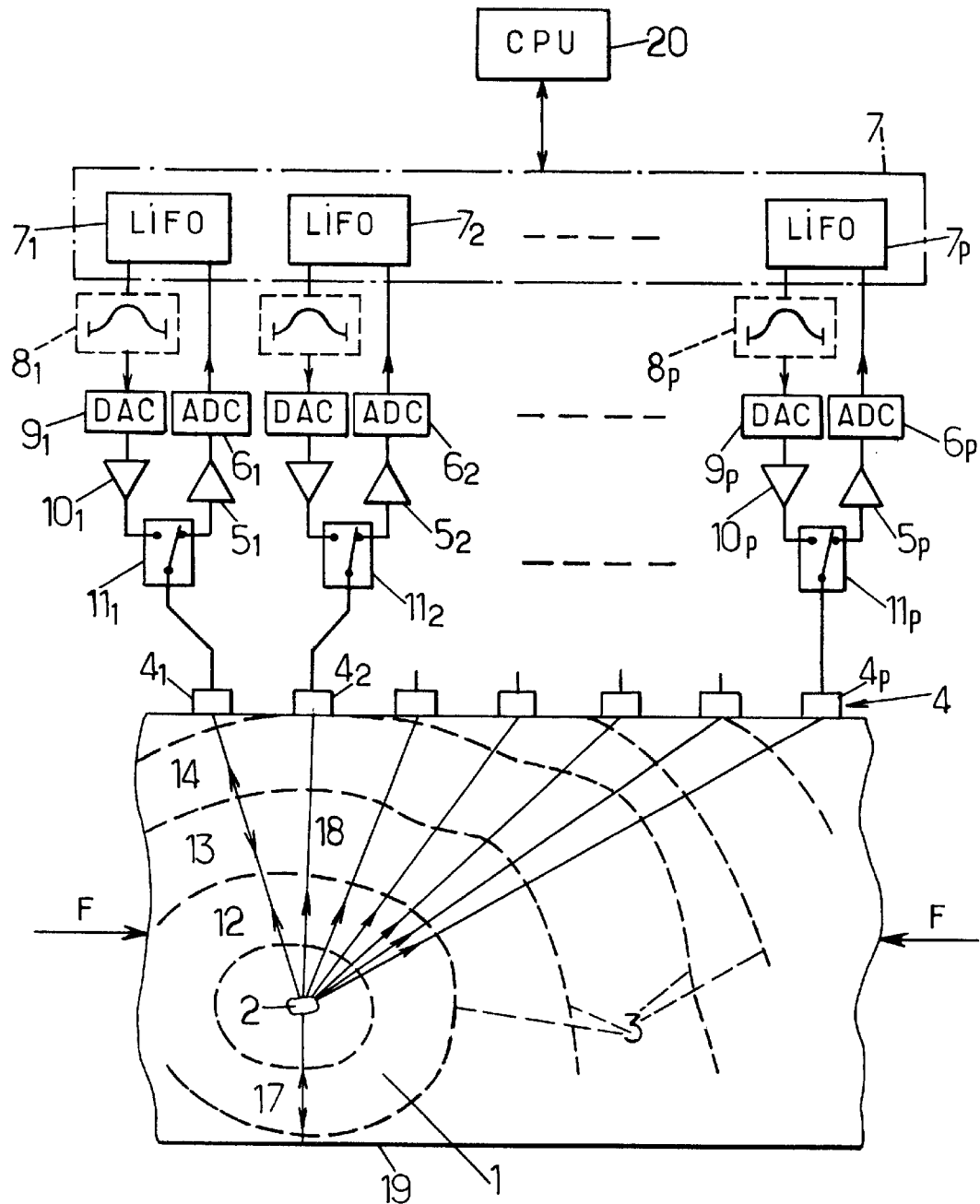
FIG. 1 is an outline diagram intended to show the elements involved in implementing the invention in its application to the non-destructive testing of articles by acoustic emission.

FIG. 1 shows, by way of example, a metallic article 1 to be tested within the scope of a non-destructive testing operation using an acoustic emission effect. Structural defects in this article are being looked for.

When it is subjected to mechanical stresses, which are schematized in FIG. 1 by the arrows F, the zones of the article 1 containing defects 2 can emit micronoise. This noise propagates along wave surfaces 3 which: in the article and reaches transducers $4_i$ (i=1, 2, . . . , p) of an array 4 of transducers which are placed on one face of the article 1.

In the embodiment considered here, the first, second, third, fourth and fifth arrays mentioned above are the same, and consist of emission/reception transducers $4_i$. The array represented is one-dimensional. Of course, this array may in the general case be multidimensional, and the emission transducers may also be different from the reception transducers. The number p of transducers results from a compromise between the performance of the device and its complexity, and depends on the application in question.

The wave surfaces 3, which are substantially spherical close to the source 2, deform during propagation because of non-uniformities in characteristics governing the propagation of the waves through the material of the article 1, for example their speed.

The electric signals output by the transducers $4_i$ during a given time interval are, after passing through protective means $11_i$, amplified by amplifiers $5_i$, digitized by analog-digital converters $6_i$, and stored in respective memories $7_i$.

In FIG. 1, the memories $7_i$ are represented, by way of illustration, as memories of the last in/first out (LIFO) type, in order to schematize the time reversal operation which the device performs. In practice, these memories $7_i$ may consist of different address zones of a single memory plane 7.

A control processor 20 supervises the operation of the device, in particular by monitoring the reading and writing in the memory 7.

The signals read from a memory $7_i$ are converted to analog form by a digital-analog converter $9_i$, then amplified by a power amplifier $10_i$. The amplified signals thus obtained are sent to the transducers $4_i$ through the protective means $11_i$. As schematized in FIG. 1, these means $11_i$ consist, for example, of electronic switches controlled by the processor 20 in order to protect the input of the amplifiers $5_i$ from the energy produced by the power amplifiers $10_i$ in the emission phases. These protective means 11 could also comprise voltage limiter devices such as diodes or dischargers.

The operation of the device is controlled by the processor 20, which follows the instructions of a suitable program parameterized by the user.

Figure 2:
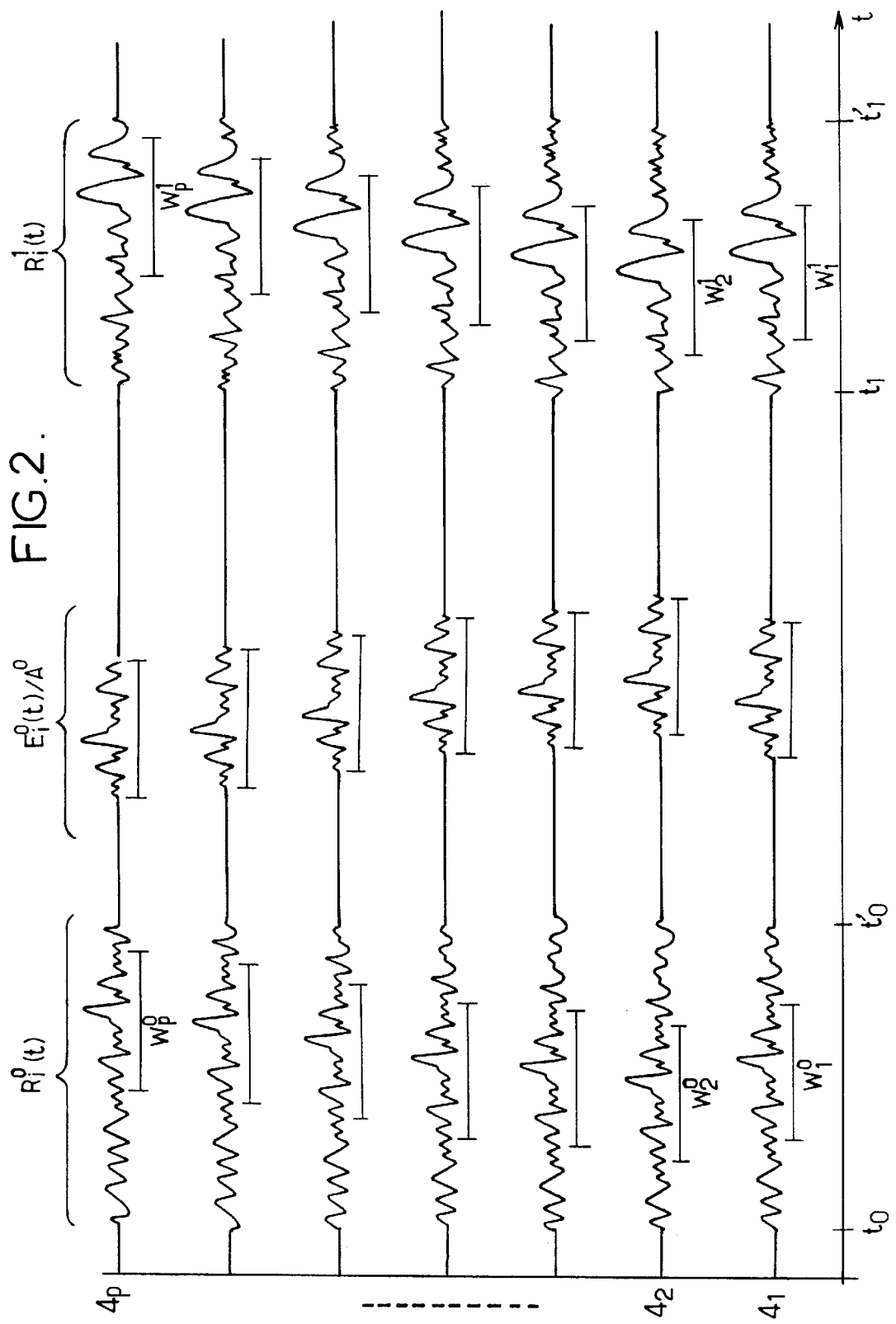
FIG. 2 is a graph schematically showing signals obtained by implementing the invention.

In an initial passive step, subsequent to the application of the stresses F, the processor 20 controls the acquisition of the electric signals delivered by the transducers $4_i$, and the storage in the memories $7_i$ of these amplified and digitized signals $R_i^n(t)$. In the example illustrated in FIG. 2, this step of acquiring the signals $R_i^0(t)$ corresponds to the time interval $[t_0, t'_0]$. It will be noted that the acquisition time intervals could differ from one transducer to another. In these signals $R_i^0(t)$, the contribution from the required sources (defects 2) may not be very distinct from the background noise.

For each transducer $4_i$ of the array 4, the processor 20 selects a time window $W_i^0$ on the basis of the position of this transducer relative to the zone being explored.

The processor 20 then controls the reading from the memories $7_i$ in order to produce time reversed digital signals $S_i^0(T^0-t)=R_i^0(T^0-t)\cdot W_i^0(T^0-t)$ at the input of the converters $9_i$. If the windowing functions $W_i^0(t)$ used are not square-wave, weighting filters $8_i$ are provided which provide the multiplications by the appropriate weighting coefficients at the input of the converters $9_i$. The time reversed digital signals correspond to the signals $E_i^0(t)/A^0$ represented in FIG. 2 in the case of square-wave windowing functions.

After conversion to analog form, the power amplifiers $10_i$ apply the amplification gain $A^0$ in order to supply the excitation signals $E_i^0(t)$ to the emission transducers $4_i$.

The transducers $4_i$ then emit a set of acoustic signals which follow the inverse path 13 of those 12 corresponding to the wave surfaces 3, and which therefore converge towards the possible source 2. Since this source is acoustically reflective, it returns a large proportion of the incident energy. These waves thus reflected follow paths 14 and are detected by the transducers $4_i$.

The fact that the signals $R_i^0(t)$ are time reversed makes it possible, even if the medium 1 is very non-uniform in terms of propagation, to ensure automatic re-focusing of the waves re-emitted by the transducers $4_i$ towards the noise source.

Furthermore, the fact of using the time-inverted signal automatically accounts for possible stray signals on a given transducer due to reflections of the waves emitted or reflected by the reflecting source 2 on acoustic impedance discontinuities in the medium 1 or at its boundaries. For example, FIG. 1 shows such wave propagation in the direction 17 which, after reflection on a surface 19 of the medium 1, propagates towards the transducer $4_2$ in the same direction 18 as the wave directly emitted by the source 2 towards this transducer.

After a time corresponding to about twice the propagation time of the acoustic waves between the array of transducers and the zone being explored, new acquisition of the signals $R_i^1(t)$ produced by the reception transducers $4_i$ is carried out. These signals include the acoustic echoes of the wave focused on the source 2 by the time reversal process, and this contribution from the source 2 may be expected to have a greater relative strength than the signals $R_i^0(t)$ obtained during the initial passive step.

In the same way as above, the processor 20 defines a time window $W_i^1$ for each transducer $4_i$ for utilization of the signals $R_i^1(t)$.

The utilization of these signals preferably includes n iterations of the process involving time reversal, re-emission and acquisition of the echo signals. After n iterations ($n \geq 0$), the signal stored relative to transducer $4_i$ is written $R_i^{n+1}(t)$.

The utilization of the signals $R_i^n(t)$ may consist in looking for the possible presence of a signal peak on a plurality of reception channels. It is also possible to look for correlations between the signals of different channels i and j, namely $R_i^n(t)$ and $R_j^n(t)$. A method as described in EP-A-0,591,061 or U.S. Pat. No. 5,428,999 may also be used.

A preferred way of detection after n iterations ($n \geq 1$) consists in calculating cross-correlation functions $C_i^n(t)$ according to formula (2), and in taking the sum of these functions for the different channels i in order to obtain an overall cross-correlation function $C^n(t)$, in which the presence of peaks is looked for in order to detect a reflecting sound source.

Figure 3:
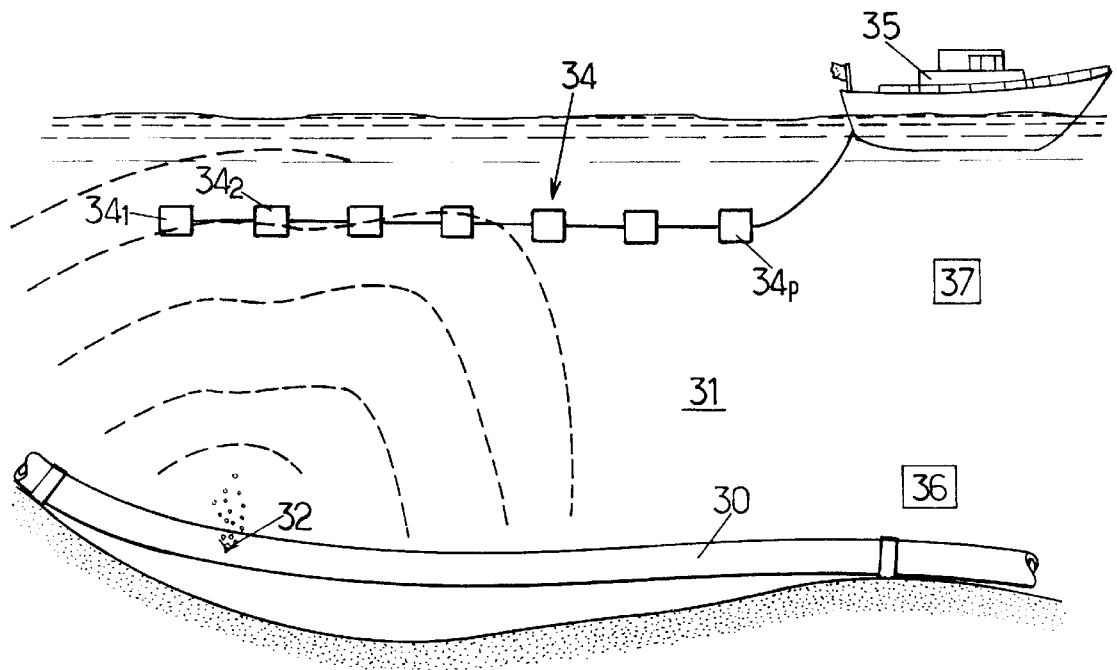
FIG. 3 is a diagram illustrating another field of application of the invention.

FIG. 3 illustrates another application of the invention, in which the propagation medium 31 is the sea and the reflecting source 32 is a gas leak in a gas pipeline 30 lying at the bottom of the water. In this case, the emission of bubbles constitutes the noise source, and the acoustic impedance discontinuity between the sea water and the bubbles and the sea water and the gas pipeline constitute the cause of reflection of the waves. The array 34 of transducers $34_i$ is here submerged. It may in particular be towed by a ship 35.

In the same way, any reflecting source such as a submarine 36 or a tethered mine 37 could be detected and located in a marine environment.

Figure 4:
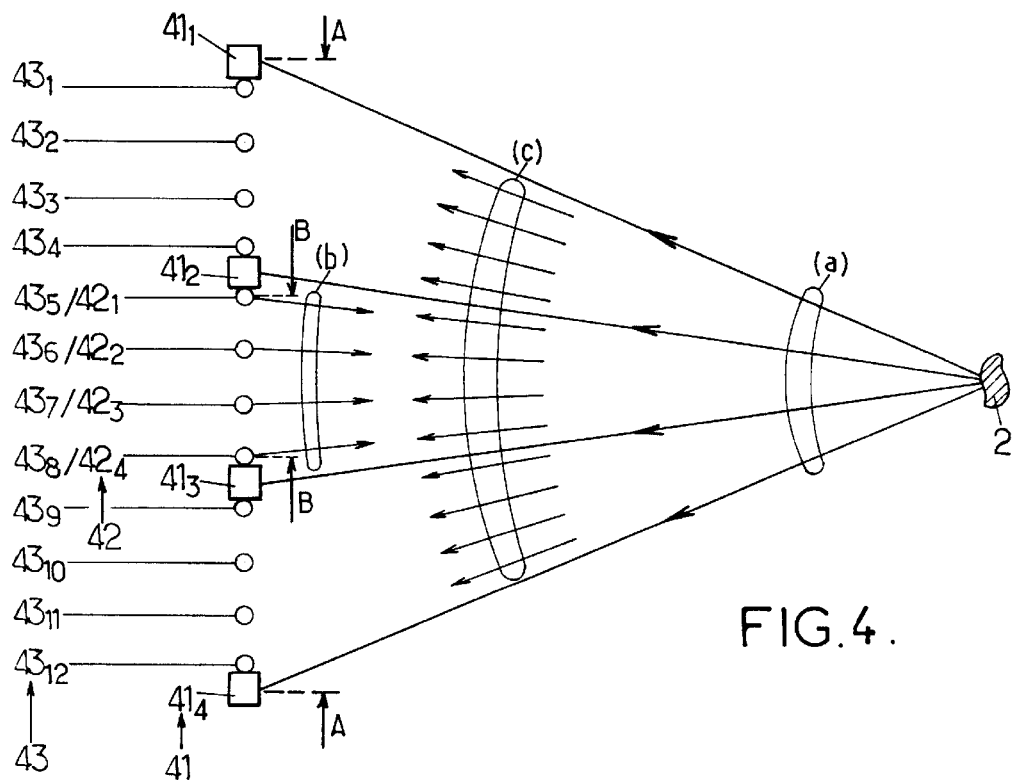
FIG. 4 is a schematic representation of an alternative embodiment of arrays of transducers which can be used according to the invention.

The invention is in no way limited to these embodiments which have been described; on the contrary, it encompasses all variants thereof. One particularly advantageous such variant is when the desire is to locate very accurately a reflecting source which generates relatively low-frequency sounds, which normally leads to a low accuracy in the location. In order to considerably improve this accuracy in the location of the reflecting source, higher frequencies are used during the emission/reception phases than those acquired in the initial passive step. To this end, the reception transducers of the first array operate at low frequency, and those of the second, third, fourth and fifth arrays of transducers (emission/reception) operate at higher frequency. An arrangement of this type is shown in FIG. 4.

During the initial listening, the p reception transducers $41_i$ of the first array 41 are distributed over a zone of lateral dimension A. The signals initially received by these transducers are processed as described above in step (a), with a time compression operation as well. The excitation signal re-emitted during the first re-emission (step (b)) thus becomes:

$$E_i^0(t)=A_i^0\cdot S_i^0(T_i^0\alpha t)$$

where $\alpha$ is a factor greater than 1 defining the ratio between the emission frequencies and those contained in the initial reception.

These signals are emitted by transducers $42_j$ distributed into the second array 42, which is tighter than the first array 41 and has lateral dimension B<A. It is advantageous to use a second array 42 corresponding to the first array 41 through a homothetic transformation of ratio $1/\alpha$. The arrays 41 and 42 comprise the same number p of transducers (in the simplified example of FIG. 4, p=4 and $\alpha \approx 4$). The signals initially received by each transducer $41_i$ (arrows (a) in FIG. 4) are sent to the corresponding transducers $42_j$ with j=i for the first re-emission (arrows (b)). The signal received at i=1 is thus re-emitted at j=1, etc.

In the preferred embodiment illustrated by FIG. 4, the third array 43 is separate from the first two 41, 42 and is composed of emission/reception transducers $43_k$ for k=1, 2, ..., q (it is merged with the "fourth" and "fifth" arrays). The arrows (c) denote the acoustic echo signals received by the transducers $43_k$ in step (c).

The array 43 has dimensions larger than those of the second array 42 (typically of the order of A), and contains more transducers: q>p. Such an arrangement makes it possible greatly to improve the accuracy of the location.

In the example represented in FIG. 4, q=12 for p=4, and the transducers $43_5$ to $43_8$ are, respectively, the transducers $42_i$, to $42_4$ of the array 42. Since the second array 42 is intended to operate at high frequency, it is actually expedient to arrange for it to be composed of emission/reception transducers which furthermore form part of the third array 43. Moreover, if broadband transducers are used, it is possible to arrange for the transducers $41_i$ of the first array 41 to also form part of the third array 43.

What is claimed is:

1. Method of detecting and/or locating a sound source by means of transducers organized in arrays comprising first, second and third transducer arrays, whereby a spatial correspondence is provided between said first and second transducer arrays, the method comprising a passive initial step in which acoustic signals received by reception transducers of the first array are sensed, and electric signals produced by the reception transducers of the first array in response to said acoustic signals are stored, wherein the passive initial step is followed by the steps of:
   (a) time reversing and amplifying at least one time window of each electric signal stored in the passive initial step in order to produce excitation signals;
   (b) applying the excitation signals to respective emission transducers of the second array;
   (c) sensing acoustic echo signals received by reception transducers of the third array, and storing electric signals produced by the reception transducers of the third array in response to said acoustic echo signals; and
   (d) using the electric signals stored in step (c) to detect the possible presence of a reflecting sound source.

2. Method according to claim 1, wherein said arrays further comprise fourth and fifth transducer arrays, whereby a spatial correspondence is provided between said third and fourth transducer arrays, and wherein step (d) of using the electric signals stored in step (c) comprises at least one iteration of a process including the steps of:
   (e) time reversing and amplifying at least one time window of each of the electric signals which have just been stored in order to produce excitation signals;
   (f) applying the excitation signals produced in step (e) to emission transducers of the fourth array; and
   (g) sensing acoustic echo signals received by reception transducers of the fifth array, and storing electric signals produced by the reception transducers of the fifth array in response to said acoustic echo signals.

3. Method according to claim 2, wherein the third, fourth and fifth arrays are merged and comprise emission/reception transducers.

4. Method according to claim 2, wherein the third and fifth arrays are merged, the method further comprising the following steps after a number n, at least equal to 1, of iterations of said process have been performed:
   evaluating an individual cross-correlation function, for each one of at least some of the reception transducers of the third array, between the electric signals stored relative to said one of the reception transducers of the third array immediately before the n-th iteration and in step (g) of the n-th iteration, respectively, and
   detecting the possible presence of a reflecting sound source on the basis of the evaluated individual cross-correlation functions.

5. Method according to claim 4, further comprising the steps of:
   calculating a sum of the individual cross-correlation functions relating to at least some reception transducers of the third array in order to obtain an overall cross-correlation function, and
   searching for the presence of a peak in the overall cross-correlation function in order to detect the possible presence of a reflecting sound source.

6. Method according to claims 2, wherein the first, second, third, fourth and fifth arrays are merged.

7. Method according to claim 1, wherein the first and second arrays are merged and comprise emission/reception transducers.

8. Method according to claim 1, wherein the excitation signals are obtained in step (a) by a time reversal operation in which frequencies contained in the signals stored in the initial passive step are multiplied by a coefficient a greater than 1, and wherein the second array of emission transducers corresponds to the first array of reception transducers through a homothetic transformation of ratio $1/\alpha$.

9. Method according to claim 8, wherein the second array consists of emission/reception transducers also forming part of the third array.

10. Method according to claim 8, wherein the third array has substantially larger dimensions than the second array and includes more transducers.

11. Device for detecting and/or locating a sound source, comprising:
   a first array of reception transducers for sensing acoustic signals during a passive initial step;
   storage means for storing electric signals produced by the reception transducers of the first array in response to said acoustic signals;
   processing means for time reversing and amplifying at least one time window of each electric signal stored in the storage means in the passive initial step in order to produce excitation signals;
   a second array of emission transducers, spatially corresponding to the first array to which said excitation signals are respectively applied; and
   a third array of reception transducers for sensing acoustic echo signals received in response to waves emitted by the emission transducers of the second array,
   wherein the storage means store electric signals produced by the reception transducers of the third array in response to said acoustic echo signals, and
   wherein the processing means are designed to use the stored electric signals order to detect the possible presence of a reflecting sound source.

12. Device according to claim 11, further comprising a fourth array of emission transducers and a fifth array of reception transducers, whereby a spatial correspondence is provided between said third and fourth arrays, wherein the processing means are designed to use said stored electric signals by carrying out at least one iteration of a process including the steps of:

(e) time reversing and amplifying at least one time window of each of the electric signals which have just been stored in order to produce excitation signals;

(f) applying the excitation signals produced in step (e) to emission transducers of the fourth array; and (g) sensing acoustic echo signals received by reception transducers of the fifth array, and storing electric signals produced by the reception transducer of the fifth array in response to said acoustic echo signals.

13. Device according to claim 11 wherein the processing means are designed to produce the first set of excitation signals by a time reversal operation in which frequencies contained in the signals stored in the initial passive step are multiplied by a coefficient a greater than 1, and wherein the second array of emission transducers corresponds to the first array of reception transducers through a homothetic transformation of ratio $1/\alpha$.

* * * * *